United States Patent [19]
Shukla et al.

[11] Patent Number: 6,057,773
[45] Date of Patent: May 2, 2000

[54] UNANCHORED SENSOR FOR FLUID CHARACTERISTICS

[76] Inventors: Ashok K. Shukla; Mukta M Shukla, both of 10423 Popkins Ct., Woodstock, Md. 21163

[21] Appl. No.: 09/094,629

[22] Filed: Jun. 15, 1998

Related U.S. Application Data

[63] Continuation-in-part of application No. 08/201,793, Feb. 25, 1994, Pat. No. 5,625,344, and a continuation-in-part of application No. 08/806,112, Feb. 25, 1997, Pat. No. 5,767,775.

[51] Int. Cl.[7] .................................................. G08B 21/00
[52] U.S. Cl. ........................ 340/623; 340/603; 340/618; 340/624; 200/61.45 R
[58] Field of Search .................................. 340/539, 521, 340/603, 618, 623, 624; 200/61.45 R, 84 R, 220, 223, 230

[56] References Cited

U.S. PATENT DOCUMENTS

| | | | |
|---|---|---|---|
| 3,603,952 | 9/1971 | Smith | 340/539 |
| 3,786,464 | 1/1974 | Staempfli | 340/623 |
| 4,878,043 | 10/1989 | Heusquin et al. | 340/521 |
| 4,886,590 | 12/1989 | Tittle | 204/232 |
| 5,053,751 | 10/1991 | Gould | 340/623 |
| 5,263,371 | 11/1993 | Maresca, Jr. et al. | 73/290 V |
| 5,264,368 | 11/1993 | Clarke et al. | 340/623 |
| 5,331,105 | 7/1994 | Suncum et al. | 585/800 |
| 5,532,679 | 7/1996 | Baxter, Jr. | 340/539 |
| 5,767,775 | 6/1998 | Shukla et al. | 340/623 |

*Primary Examiner*—Jeffery A. Hofsass
*Assistant Examiner*—Van T. Trieu

[57] ABSTRACT

A device and method for sensing fluid characteristics, including, temperature, pH and chemistry, comprises a switch affixed to or embedded in a container of a size, shape and density such that said container floats stable in said liquid sensors which measure and report other characteristics of the liquid, such as temperature, pH, viscosity, chemistry or biochemistry.

19 Claims, 2 Drawing Sheets

UNANCHORED SENSOR FOR FLUID CHARACTERISTICS

RELATED APPLICATION

This application is a continuation-in-part of U.S. Application, Ser. No. 08/201,793 filed on Feb. 25, 1994 now U.S. Pat. No. 5,625,344 and 08/806,112 filed on Feb. 25, 1997 now U.S. Pat. No. 5,767,775.

FIELD AND BACKGROUND OF THE INVENTION

This invention relates to an unanchored device and method for sensing and measuring fluid characteristics, including fluid level, temperature, pH and chemical and biochemical properties. After the characteristics of the fluid are detected and/or measured they are wirelessly transferred to receivers which in turn can perform functions such as alerting, data processing or controlling other devices.

BACKGROUND INFORMATION

The determination of fluid characteristics can be very useful for many processes. For example, pH levels are routinely monitored during processes such as fermentation and in many other applications in chemical or biological research labs. The current pH measuring methods depend on the connection of the probe to the pH meter by a wire. However, the presence of the wire complicates pH measurements in many experimental situations. The sensor described herein can provide a wireless detecting system for measuring pH levels. Additionally, such a sensor could be used to simultaneously detect other fluid characteristics such as temperature chemical and biochemical properties.

Most commercially available pH-sensors and other ion-specific electrodes or chemical specific electrodes are connected by a wire to a control or measurement device. This restriction tends to limit the applications of such detection devices. For example, the physical size of many small containers or the small volume of liquid in many experimental situations does not permit the use of current detection devices.

Considering all the detecting systems currently available, the invention described herein has the following advantages:

Small size

Does not depend on the type of container; it can be used with virtually any container.

Autoclaveable

Can be made of solvent inert materials such as TEFLON™.

Can be used to measure multiple parameters such as temperature, pH

The principal objective of this invention is to provide a simple sensor for the determination of fluid characteristics and this sensor can wireless transmit a signal and data to a receiver, which can process the data or immediately interrupt the function of different devices used in the process. One of the advantages of such an automated system is that it avoids errors associated with human operation or control. Furthermore, this sensor can measure other parameters beside pH, such as the fluid level or temperature in a reaction chamber or fermentor, and it can transmit the combined data to a data processor or control unit. The control unit, in turn, can perform a spectrum of desired operations in response to the data transmitted by the receiver. The sensor should be made of a material such as TEFLON™, which is inert to most solvents. This unit can be used in fluids of different densities and viscosities.

SUMMARY OF THE INVENTION

It is an object of this invention to provide an unanchored sensor for the detection of fluid characteristics which does not rely on a wire-based or any other type of permanent connection that may impose restrictions on the applications of the detection or measurement processes.

The various features of novelty, which characterize the invention, are pointed out with particularity in the claims annexed to and forming a part of this disclosure. For a better understanding of the invention, its advantages and objects, reference is made to the accompanying drawings and descriptive matter in which a preferred embodiment of the invention is illustrated.

BRIEF DESCRIPTION OF THE DRAWINGS

The foregoing and still other objects of this invention will become apparent, along with various advantages and features of novelty residing in the present embodiments, from study of the following drawings, in which.

DESCRIPTION OF THE PREFERRED EMBODIMENT

Figure 1A:
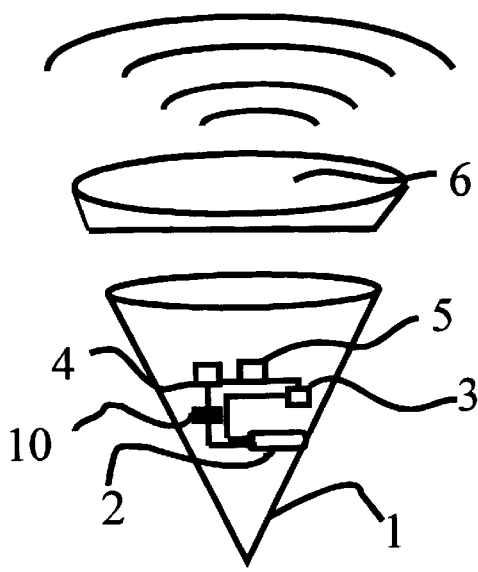
FIGS. 1a and 1b are an expanded view of one embodiment of a device according to the present invention.

Referring to the drawings, the invention is a device (1) FIG. 1a, which is not anchored to the container and can either float on the surface of fluid or be suspend within the fluid or sink to the bottom of the container. The sensor (2) contained within the device can measure the characteristics of the fluid continuously or in specific intervals and send the data to the receiver (7), which can display the data transmitted by the sensor or perform secondary controlling or processing functions. The device (1) can be made of any shape or size and can be made of any material although inert materials such as TEFLON™ which do not react with the fluid would be preferred. The data transferred from the sensor to the receiver can be transmitted by a transmitter (3). The device can also have a frequency generator (10) (FIG. 1.). The data can be transmitted through a radio frequency or 900 mega hertz-range or any other frequencies including ultrasound, light emitting diodes, infrared diodes and UV-light.

The device (1) is powered by a battery (4), which may be in series with a switch (5). The circuit may contain an inductive coil or a frequency transponder with a switch but without a battery (the activation energy for the transponder or inductive coil will be received from a receiver or an out side source), to transmit the signals to the receiver. The entire unit can be a sealed capsule in which the interior components are molded into the unit. Alternatively, the device can be sealed with a cap (6) as is shown in FIG. 1a. The cap can be either permanently sealed onto the device or it can be removable such as to permit battery (4) changes and other manipulations to the device such as changing the alarm device and circuitry or adding other components.

Figure 2:
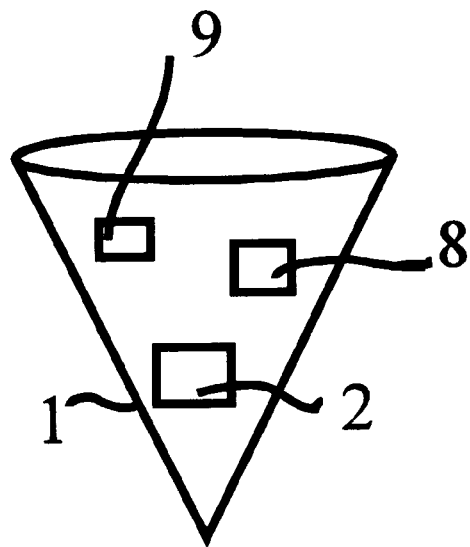
FIG. 2 is an enlarged view of the portion of FIGS. 1a and 1b compressing the schematic view of the sample circuit diagram with additional sensors.

Furthermore, as is shown in FIG. 2, other sensors (for example, pH, temperature, viscosity, enzyme, affinity, ion, conductivity, chemical, biochemical and gases, dissolved in fluid, sensor) (8, 9) can be attached to the same circuit containing the original sensor (2) or in separate circuits. These sensors can be specified for detecting or measuring temperature, pH, enzyme levels or activity, ions and many other chemical or biochemical fluid characteristics.

Figure 3:
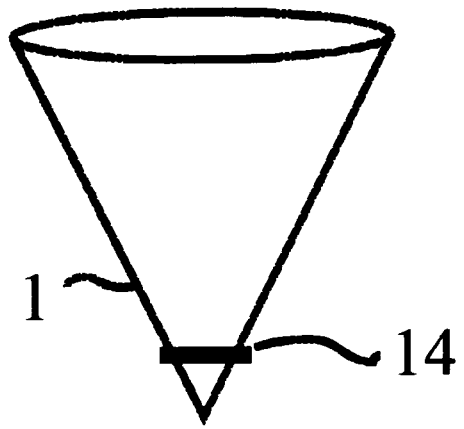
FIG. 3 is an expanded view of the device showing the built in magnet.

These sensors can be programmed to be in activation either continuously or only at regular intervals. The activation can be achieved electronically by sending an electronic impulse (radio frequency, etc.) from an external source or mechanically by physical processes such as stirring or by using magnetic or electromagnetic field. Furthermore, for starting and stopping processes a switch (5) can be used where such a switch is activated by the use of a magnetic switch and or a level switch. For instance, a sensor built into a magnetic stirrer can start sending the signal once stirring is initiated and stop when stirring is interrupted or discontinued. A magnetic rod (10) (FIG. 3) can be attached to the device (1) to enable rotation when placed on a magnetic stirrer plate, for a better mixing of the solution.

The device (1) can be used for data collection as well as an alarm device. Such an alarm device could transmit a signal as soon as a desired value for pH, temperature or any other parameter is achieved. The device (1) will send a signal to a receiver and can also activate an alarm, which can be based on different signals such as light, sound a frequency or a combination of the above signals.

Figure 1B:
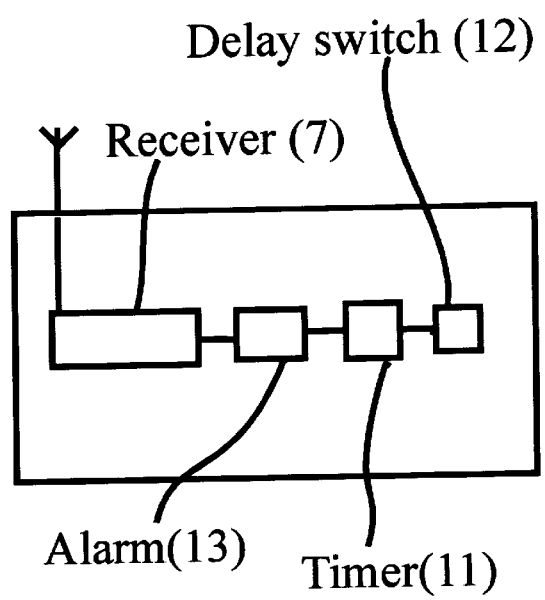

The alarm (13) as in FIG. 1b can be designed to simply alert a human operator of the lower or upper limits of the fluid characteristics, or it can be coupled with other devices to perform remedial actions such shutting off a pump or a heat source. The alarm (FIG. 1b) can also be coupled to a timer (11) or delay switch (12) so as to take automatic remedial action if a human operator does not intervene within a predetermined time period. If the signals from the device (1) are weak, they can be further amplified before being sent to a receiver or a controlling device by another external device which can be remotely controlled or connected by a wire. The latter process can be useful in the case of metallic or opaque containers or in instances where the device is significantly distanced from the receiver.

Furthermore, more than one device (1) can be placed in a container and different transmission frequencies can be transmitted by different sensors for different operations.

Furthermore, different frequencies can be programmed in different sensors so that many sensors can be operated in the same area. Thus, one or more sensors can be placed in the same container for the determination of different properties of fluids.

The broader usefulness of the invention may be illustrated by the following examples.

EXAMPLES OF APPLICATIONS

Example #1 Remote Controlled pH meter.

A pH meter probe can be placed in the device (1). The pH can be measured and the value transmitted to a receiver for control. Such device would be useful for pH measurements during fermentation or other processes.

Example #2 Remote controlled enzyme reactions.

Probes such as biosensors of different types (for example for oxygen, nitrogen, enzyme, alcohol, glucose or substrates or products of enzyme reactions) can be included in the device and can be used to measure fluid characteristics and transmit data directly to a control or warning unit. More than one biosensor can be used in a single device and each probe can send a signal to one or more receivers, which can control and process results simultaneously.

While a specific embodiment of the invention has been shown and described in detail to illustrate the application of the principles of the invention, it is understood that the invention may be embodied otherwise without departing from such principles and that various modifications, alternate constructions, and equivalents will occur to those skilled in the area given the benefit of this disclosure and the embodiment described herein, as is defined by the appended claims.

What is claimed is:

1. An unanchored sensing device for immersion or suspension in a liquid, said device comprising a sensor for sensing a characteristic of said liquid and a transmitter for transmitting information concerning said characteristic to a receiving device for receiving said information, said receiving device being external to said liquid said transmitter having a magnet material rod for stirring of liquid.

2. An unanchored sensing device as in claim 1 wherein said sensor is selected from the group of sensors consisting of pH, temperature, viscosity, enzyme, affinity, ion, conductivity, chemical, biochemical and gases.

3. An unanchored sensing device as in claims 1 or 2 wherein said sensor comprises plurality sensors in said device.

4. An unanchored sensing device as in claim 1, wherein said transmitter comprises a frequency generator.

5. An unanchored sensing device as in claim 4 wherein said frequency generator is a radio frequency or 900 mega hertz range source.

6. An unanchored sensing device as in claim 4 wherein said frequency generator is an infrared light source.

7. An unanchored sensing device as in claim 4 wherein said frequency generator is a sound source.

8. An unanchored sensing device as in claim 4 wherein said sound source is an ultrasound source.

9. An unanchored sensing device as in claim 1 or 4 further comprising a control device with built-in alarm signal device.

10. An unanchored sensing device as in claim 4 further comprising a timer for delaying activation for a predetermined period of time or time intervals.

11. An unanchored sensing device as in claim 1 further comprising circuitry for activating an alarm device, which is activated when predetermined value is achieved.

12. An unanchored sensing device as in claim 1, where said receiver can have an alarm device.

13. An unanchored sensing device as in claim 1, where said receiver have processing capabilities.

14. An unanchored sensing device as in claim 1, where said receiver is a transreceiver.

15. An unanchored sensing device as in claim 1, where said transmitter is a transreceiver.

16. An unanchored sensing device as in claim 1, where said transmitter is a transponder.

17. An unanchored sensing device as in claim 1, where said receiver have a delay switch.

18. An unanchored sensing device as in claim 1, where said transmitter have a battery.

19. An unanchored sensing device as in claim 1, where said transmitter have a switch for activating or deactivating the device, said switch is selected from the group consisting of electrical, mechanical, magnetic and electromagnetic switch.

* * * * *